United States Patent [19]

Gershman et al.

[11] Patent Number: 4,665,553
[45] Date of Patent: May 12, 1987

[54] METHODS AND APPARATUS FOR ANALYSIS OF PARTICLES AND CELLS

[75] Inventors: Russell J. Gershman, Middleborough; Robert A. Hoffman, Mansfield; J. Garland O'Connell, Newtonville, all of Mass.

[73] Assignee: Ortho Diagnostics Systems Inc., Raritan, N.J.

[21] Appl. No.: 605,732

[22] Filed: May 1, 1984

[51] Int. Cl.$^4$ ............... G01N 33/48; G06K 9/00
[52] U.S. Cl. ............... 382/6; 350/358; 350/380; 356/39; 356/338; 382/48
[58] Field of Search ............... 356/337–343, 356/39; 350/380, 358; 364/416; 382/6, 66, 48; 377/10, 11; 250/205; 235/455

[56] References Cited

U.S. PATENT DOCUMENTS

| | | | |
|---|---|---|---|
| 3,399,013 | 8/1968 | Aas et al. | 350/358 |
| 3,435,228 | 3/1969 | Gordon | 350/358 |
| 3,507,553 | 4/1970 | Anderson et al. | 350/358 |
| 3,524,011 | 8/1970 | Korpel | 350/358 |
| 3,785,735 | 1/1974 | Friedman et al. | 356/343 |
| 3,873,974 | 3/1975 | Bouton et al. | 382/6 |
| 4,125,828 | 11/1978 | Resnick et al. | 382/6 |
| 4,207,554 | 6/1980 | Resnick et al. | 382/6 |
| 4,267,439 | 5/1981 | Thomas et al. | 235/455 |
| 4,284,412 | 8/1981 | Hansen et al. | 356/39 |
| 4,513,438 | 4/1985 | Graham et al. | 382/6 |

OTHER PUBLICATIONS

M. J. Eccles, "A Programmable Flying-Spot Microscope and Picture Preprocessor", 1–76.

*Primary Examiner*—Leo H. Boudreau
*Attorney, Agent, or Firm*—Audley A. Ciamporcero, Jr.

[57] ABSTRACT

Samples are prepared and applied to a cuvette, and the cuvette is translated in a given direction. Laser light is coupled to the sample through a Bragg cell, which causes the beam to scan the sample transversely to the given direction. Select optical parameters are monitored, and when they occur, the scan is stopped or slowed for a more complete analysis of the illuminated cell.

13 Claims, 3 Drawing Figures

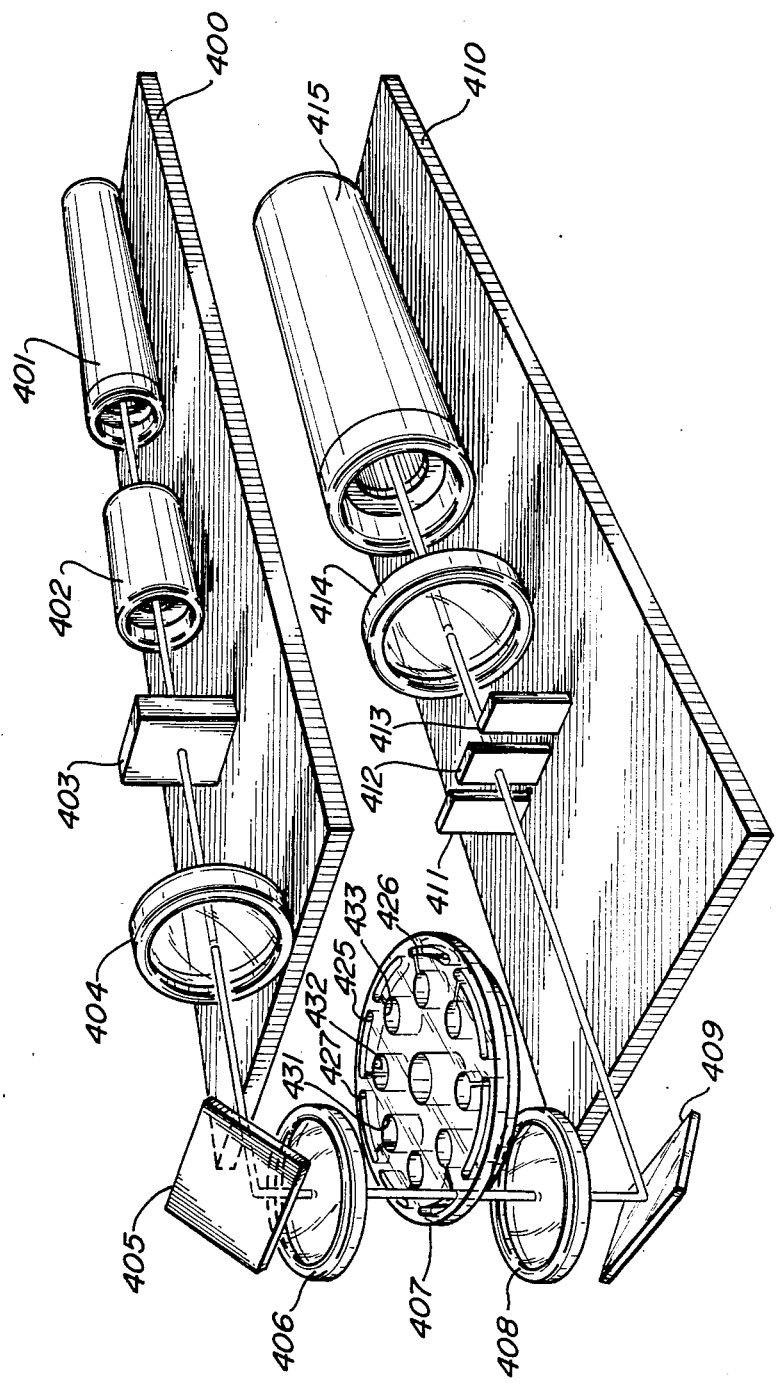

METHODS AND APPARATUS FOR ANALYSIS OF PARTICLES AND CELLS

FIELD OF THE INVENTION

This invention relates to particle and cell analysis, and more particularly to low-cost high speed optical techniques for determining the characteristics of individual particles and cells in a medium.

BACKGROUND OF THE INVENTION

In the 70's, the advent of optical and impedance-based measurements permitted for the first time relatively rapid automated sizing, counting, and allied investigations of individual cells. Impedance-based systems, in which cells were caused to proceed through an orifice, are based on the proposition that certain cell parameters, principally related to size, correlate with changes of impedance at the orifice as cells pass therethrough. Competing with the impedance systems were early optical flow cytometry systems, in which hydrodynamic principles were utilized to pass cells rapidly, substantially one at a time, through a zone of focused illumination such as that from a laser beam. Each cell interacts characteristically with the beam, and depending variously on light extinction, narrow and wide angle scanner, and back scatter (i.e., reflection), computation algorithms allowed for substantial discrimination among cell types based on these optical interaction parameters. See, for example, U.S. Pat. Nos. 3,662,176 to Kamentsky et al., 3,785,735 to Friedman et al., and 3,705,771 to Friedman et al.

After a time, principles of optical flow cytometry were adapted to ever-increasingly sophisticated approaches to analysis. Dyes such as acridine orange, which fluoresce in the presence of certain types of illumination, were found to be taken up in different proportions by different types of cells depending on their pathological and morphological character. See, for example, U.S. Pat. No. 3,684,377 to Adams et al.

Thus, while impedance-based and optical flow cytometry systems competed vigorously for predominance in the clinical marketplace, the optical systems found favor and acceptance in research laboratories, wherein relatively high instrument costs, and the associated elaborate processing and preprocessing steps were easily outweighed by the powerful and extensive information which could be learned on a cell-by-cell basis. In fact, several major manufacturers came to offer elaborate, powerful optical flow cytometry systems directed to the research laboratory marketplace, in which plural lasers were utilized in conjunction with a variety of sample processing and dyeing techniques, and wherein elaborate algorithms allowed the basic optical interaction parameters (i.e. extinction, back scatter, narrow angle scatter, wide angle scatter, and plural color fluorescence) to assemble highly accurate data regarding subpopulations of cells in the sample. Prime examples of these types of instruments are those offered under the brand name CYTOFLUOROGRAF ® by Ortho Diagnostic Systems Inc., Raritan, N.J., and its predecessors in interest.

Optical flow cytometry instruments therefore enjoyed an important role in the development of modern immunology and immunologically based reagents such as those utilizing monoclonal and polyclonal antibodies. Earlier immunologic experiments were premised on elaborate incubation and manual counting and analysis techniques, as well as manual achievement of physical isolation of respective subclasses. Along the way, however, it was determined that optical flow cytometry techniques could vastly attenuate the duration of such experiments by providing analysis and sorting on an automated basis. Thus, the very development of monoclonal antibodies and the like reagents occurred hand in hand with the continuing refinement of optical flow cytometry techniques and apparatus. Moreover, as the various antibody secreting hybridoma cell lines were developed, and their characteristic antibodies became available, the optical flow cytometry systems became a modality of choice for use of the antibodies for diagnostic, monitoring, and the like purposes. For example, Ortho Pharmaceutical and Ortho Diagnostic Systems Inc., both of Raritan, N.J., have developed a series of monoclonal reagents under the "OKT" ® trademark, which react selectively with human T-lymphocyte cells. These monoclonal antibodies are capable of carrying markers which fluoresce in the presence of select illumination, and hence offer the capability of cellular analysis and sorting in optical flow cytometry systems. U.S. Pat. No. 4,284,412 to Hansen et al. describes and claims methods and apparatus for automated identification and enumeration of blood cell subclasses, such as human T-cell subclasses, through the use of optical flow cytometry systems. The assignee hereof, which is also the assignee of the Hansen et al. patent, offers commercially a line of systems under the SPECTRUM trademark which is designed in part for these immunologic techniques. Other manufacturers as well, have commercially offered antibodies and instruments which they claimed are the equivalents of Ortho's reagents and systems.

Thus, the sciences of immunology and cell analysis instrumentation have been developed in a partnership, without which it is doubtful that either would have advanced to its present state. The associated difficulty, however, is that the optical flow systems are relatively expensive, and their elaborate optical and hydrodynamic systems are mechanically complex and sensitive, and therefore tend to be service intensive. Thus, while there is a strong need to move immunologic analyses to everyday use in the clinical laboratory, progress tends to be impeded by the overall system cost and the high level of effort required to maintain system accuracy and reliability. Further, there is a standing need to have test formats and procedures which require minimal operator sophistication, which object is not always met in modern optical flow cytometry immunologic testing techniques.

It is, accordingly, a primary object of the present invention to provide apparatus and techniques which improve upon and simplify present optical techniques for immunology and hematology. It is a further object to provide instruments for such analysis which are low in cost, high in reliability, and which require minimal sophistication on the part of the operator.

SUMMARY OF THE INVENTION

Legendary bounty hunters in the Old West were known to attribute their success to, "looking where they are, and not where they ain't". In essence, the principles of the present invention apply the "looking where they are" rationale to automated immunology and hematology instrumentation, by scanning samples in a medium at a very rapid rate, looking for one or more key select parameters which indicate presence of a cell in question, and upon detection of each cell, there is conducted a more complete monitoring of all relevant parameters with respect to that cell, for example, by halting or slowing the scan while optical parameters are measured. Thereupon, the scan continues.

Taking this approach results in more accurate analysis of weak signals than for flow cytometry systems, in which flow rate must be slowed in order to retain or improve sensitivity, because flow systems are limited by the hydrodynamic flow rates to deliver cells one at a time to the stationary illumination zone of focused laser light. In accordance with the principles of the present invention, the laser light is caused actually to seek the cells, and to inquire individually of them as to the relevant parameters.

In some measure, the principles of the present invention are facilitated by use of a Bragg cell to conduct rapid deflection of a stationary laser beam, thereby to scan an area of a medium containing the cells to be investigated. Hence, in preferred embodiments, a stationary laser beam is coupled to a Bragg cell, which is a crystal having its index of refraction modulated by ultrasound energy applied from attached transducers. The modulated index of refraction causes the beam to be deflected at a predetermined angle dependent on the frequency of applied ultrasound, and appropriate focusing optics causes this scan to view a predetermined dimension of the sample medium. Intensity of the light is variable through variation of the amplitude of the applied ultrasound energy. In such preferred embodiments, the prepared samples in a cuvette or the like are moved transversely to the scanning laser beam, preferably normally thereto. Optical sensors are appropriately positioned for detecting relevant interaction of the laser beam with the cells, for example sensing light extinction, narrow angle scatter, wide angle scatter, back scatter or reflection, and fluorescence.

In preferred embodiments, one or more of these interaction parameters are monitored as the scan continues. Which one or ones of the parameters are monitored will, of course, be dependent on the sort of cell being investigated, and its characteristic interaction with the laser beam. In any event, detection of a select combination of one or more such parameters, indicating presence of a cell in question, is utilized to cause the system then to detect the other relevant parameters regarding that cell. In preferred embodiments, the Bragg cell is caused actually to halt the laser beam on the cell in question while the succeeding parameters are detected, but it is foreseen that in alternative embodiments, a slower scan rate or continuing rapid scan may continue, while the further relevant parameters from the cell are read or detected. For instance, the capacity or facility so to read the parameters "on the fly" may depend on the development of very intensely responsive dyes for generating appropriate fluorescent signal.

It may also be appropriate for certain cells or certain circumstances to provide optimization routines whereby the laser beam will substantially be centered on the cell before the relevant optical interaction parameters are detected or monitored. In an alternative embodiment, such routines may well utilize a second Bragg cell, scanning the beam transversely to the first and energized selectively when the beam is in the region of a cell to be monitored. Statistical routines premised on combinations of Bragg cells and lateral translations may also be utilized.

In preferred embodiments, the reagents and the dye preparations therefor will develop with the art and be amenable to incorporation with the principles of the present invention. Present examples, however, include the aforementioned OKT brand of monoclonal antibody reagents, stained with a phycobiliprotein dye in accordance with the teachings of a publication entitled "Fluorescent Phycobiliprotein Conjugates for Analyses of Cells and Molecules", by Oi, Glazer, and Stryker in *The Journal of Cell Biology*, Vol. 93, June 1982, pp. 981-986. Such dyes fluoresce in the red light wavelength region when illuminated with red light. Thus, a helium neon laser will be incorporated in embodiments of the present invention for such interaction. By intention, there results a highly reliable, quite inexpensive instrument, inasmuch as the relatively low power, high reliability helium neon lasers are among the least costly in the marketplace, and involve enhanced considerations of safety and the like.

It is, therefore, a primary feature of the present invention that rapid immunology and hematology measurements may be taken, a cell at a time, in a very inexpensive, reliable, and efficient system, which beneficially utilizes state of the art reagents and dyes. Ancillary features include relatively simple protocols and procedures whereby the most esoteric of diagnostic tests may be performed with facility by relatively unskilled technicians in the clinical laboratory.

DESCRIPTION OF THE DRAWINGS

FIG. 3 shows an alternative embodiment of the principles of the present invention.

DETAILED DESCRIPTION AND BEST MODE

Figure 1:
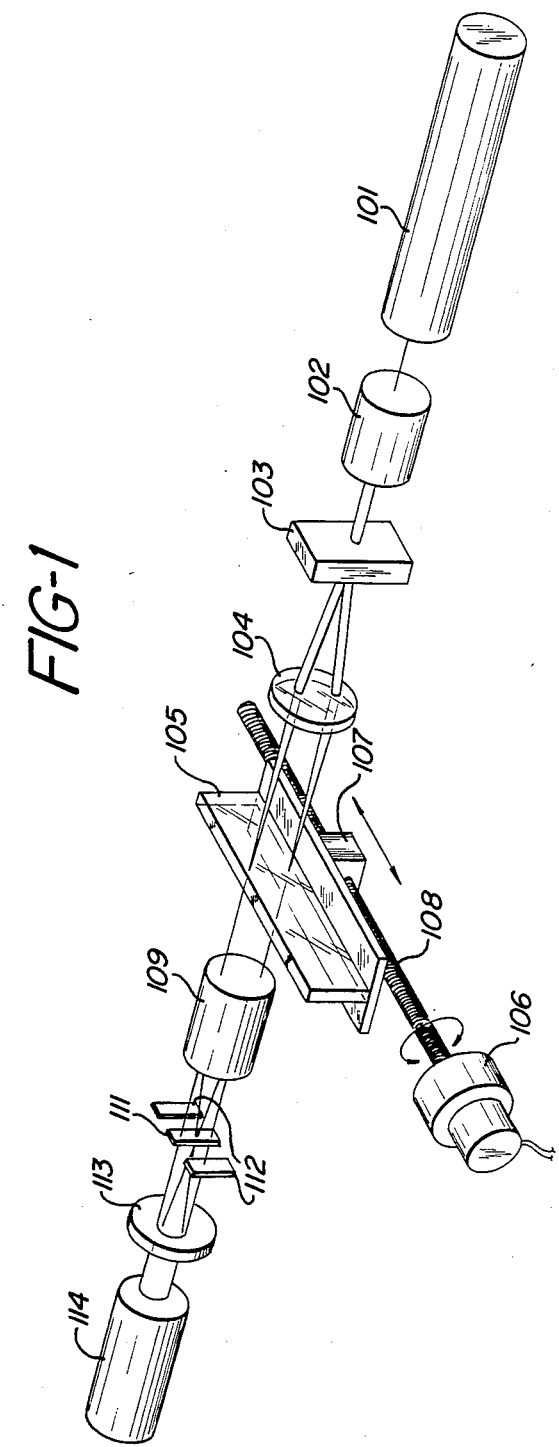
FIG. 1 shows in schematic form an illustrative embodiment of the principles of the present invention.

Referring first to FIG. 1, there is shown a preferred embodiment of the principles of the present invention. In FIG. 1, a laser 101, for example a helium neon laser, couples light to a lens or lens system 102 which expands the laser beam to create a spot of appropriate character for scanning. Light from lens system 102 is coupled to a scanning mechanism 103, preferably a single Bragg cell, but alternatively a pair of respectively orthogonal Bragg cells. Ultrasound energy applied to the extremes of the Bragg cell therefore causes a deflection of the light from the lens 102, which deflection is scanned through the angles shown in FIG. 1. Inasmuch as the scanned beam from the Bragg cell or cells 103 is radially directed, another lens 104 deflects the beams and causes all to be substantially parallel to one another.

Bragg cells suitable for use in accordance with the principles of the present invention are manufactured by Matsushita Co. of Japan, and distributed in the United States under the trademark INRAD by Interactive Radiation Inc., 181 Legrand Avenue, Northvale, N.J. Another suitable cell is marketed under the Isomet brand by Isomet Corp. of Springfield, Va. Both companies offer a variety of devices of specification suitable for the optical systems described herein.

Beams from the parallelizing lens 104 are focused upon a cuvette 105 which carries samples, and which in turn is driven transversely to the direction of scanning of the beam. As shown, the beam is normal to the cuvette. In fact, that angle of incidence of the beam may also be oblique. Herein, the term "tranverse" is used to encompass any such angle. In particular, in FIG. 1, a motor 106 turns a screw 108, upon which platform 107 is translated, in turn translating the sample cuvette 105 which is carried thereon. In preferred embodiments, this translation of the sample 105 by motor 106 occurs at a continuous, predetermined rate, while the beam is scanning the sample normally thereto at a much greater rate. As a consequence, the sample is scanned in a band defined by the laser beam scanning in the one direction (i.e., vertical), and the physical lateral translation of the sample in the other (i.e., horizontal). Of course, those of ordinary skill may wish, for some applications, also to vary the rate of such translation.

Light passing through the sample cuvette 105 is collected by a collection lens 109, and coupled to sensors which monitor or detect the interaction of the laser beam with cells of the sample in the cuvette 105. In particular, a centrally located sensor 111 monitors extinction and narrow angle scatter of light by cells of the sample, and scatter sensors 112 monitor the amount of light which has been scattered more widely by cells on the cuvette. Thus, the narrow angle sensor 111 and the wide angle sensors 112 together provide the capacity to measure extinction and wide and narrow angle scatter of light impinging on cells or particles at the sample 105.

The apparatus of FIG. 1 also shows capacity for measuring fluorescence, principally by means of one or more color filters 113, and associated photodetector or detectors 114. For example, if the laser 101 is a red light helium neon laser, and cells in the sample are prepared with a dye which emits red fluorescence when stimulated by red light, filter 113 will be designed so as to permit only fluorescent light to impinge on the photodetector 114. In the event of multiple color fluorescence emissions, there will of course be required a corresponding multiplicity of photomultiplier tubes 114 and filters 113.

It is to be understood that while the principles of the present invention employ sensors 111, 112, 113, and 114 for monitoring and detection of signal resulting from interaction of the laser light with the cells, the mechanisms embodying such apparatus are conventional, and in preferred embodiments are constituted simply of like detection apparatus from flow cytometry systems. The sensor 111 represents a conventional extinction and/or back scatter sensor. The sensors 112 represent conventional angular scatter sensors, with the separation between sensor 111 and sensors 112 determining whether relatively narrow angle or relatively wide angle sensing is to be accomplished. Clearly, in order for all of the sensors to work most efficiently with one another, conventional optics involving dichroic mirrors, beam splitters, and the like may be utilized in order to meet the logical imperatives of the system. The optical system shown, in which detector 114 is behind sensors 111 and 112, provides adequate fluorescence for beneficial operation in accordance with the principles of the present invention. Further, the precise relative physical sizes of the various sensors, while shown symbolically in FIG. 1, will vary in accordance with the needs of designers of ordinary skill. In all events, however, the design of the sensing elements is well within the level of ability of those of ordinary skill in the art.

In an illustrative embodiment, the motor 106 causes the sample 105 to translate at a rate of 0.001 microns per microsecond, while the Bragg cell 103 is causing the sample to be scanned at a rate in the range of 1 to 10 microns per microsecond. Thus, it will be seen that the vertical scan is very substantially more rapid than is the horizontal "scan" or translation, and in fact on a relative instantaneous basis, the sensors 111, 112, 113, and 114 "see" the moving cuvette as being stationary relative to the very rapid vertical scan. Moreover, even if the cells or particles of the sample are not fixed thereto, and even if the sample is vertical as shown in FIG. 1, floating or drifting of the cells on the sample normally occurs at the rate of $10^{-6}$ microns per microsecond, which is quite slow even compared to the rate of translation. Thus, at these rates, even free floating cells on the cuvette 105 may be deemed to be stationary from the standpoint of rates both of vertical and horizontal scan of the like beam.

It will be noted that the beam emergent from the laser 101 and the beam expander lens 102 is a spot essentially of Gaussian distribution, with peak intensity in the center, falling off in Gaussian fashion radially thereabout. Other than initiating scanning, the Bragg cell 103 does not substantially change this function. Hence, in simplest embodiments, wherein but a single Bragg cell 103 deflects and scans the beam in one direction (e.g., vertical), and linear translation accounts for scanning in the transverse direction, it may be desirable to incorporate provision for centering the beam on the cell prior to detailed investigation. In such event, the second, transverse Bragg cell (with associated optics) may be additionally employed at 103 for producing a limited horizontal scan of the beam once the vertical Bragg scanning has indicated presence of a cell, thus to fine tune the location of the beam on the cell, and to have the highest intensity of illumination available for optical interaction with the cell. The FIG. 1 embodiment is somewhat stylized as shown, and in the event that dual Bragg cells are to be employed, the block 103 is understood to represent both such Bragg cells.

In operation then, once the cells have been prepared on the cuvette 105 for analysis, the system is energized and the cuvette is translated in the horizontal direction shown. Meanwhile, the frequency of ultrasound applied to the Bragg cell is varied, causing the laser beam to be scanned up and down in the vertical direction, while a predetermined one or ones of the sensors are conditioned to receive signals. Which one or ones are so selected will of course depend on the type of cells under investigation. For example, presence of lymphocytes could primarily be detected through the forward scatter detector 111, whereas granulocytes could primarily be detected at the wide angle scatter sensors 112. In any event, occurrence of an optional value of this key select parameter, indicating optimal illumination of the cell in question on the cuvette 105, is utilized to stop the change of frequency of ultrasound signals at the Bragg cell 103, and hence to maintain the laser spot at that point. Thereupon, the signal available at all the sensors is detected, and correlated to indicate characteristics of the cell under investigation. This halt occurs for a predetermined time, for example for times slightly in excess of the dye bleaching time, that is the time during which fluorescent signal is available. Thereupon, vertical scanning of the Bragg cell 103 is reinstated, and the search continues for still other cells. It will be noted that in preferred embodiments, the vertical scan of the beam by the Bragg cell was halted, whereas the lateral translation of the whole cuvette, being much slower, continued unabated. During the scanning or monitoring phase of the analysis it may be desirable to change the intensity of the transmitted laser beam by varying the amplitude of the applied ultrasound. For example, dye bleaching during scanning can be reduced by such utilization of lower intensity during the scan, and increased intensity during the monitoring of the rest of the parameters.

It will therefore be apparent that the cuvette 105 has few critical parameters in accordance with the principles of the present invention. Generally, these relate simply to the ability to hold a resonable amount of sample, and to be nonreactive with light from the laser, and transmissive of such light to the collection lens 109. In its simplest form, then, the cuvette 105 may be, as shown, a pair of microscope slides bonded together and holding the sample therebetween. A more complex embodiment is shown hereinafter. In preferred embodiments, the depth or thickness of the sample, from the standpoint of light transmissivity, will be in the range of 20 cell diameters.

It is to be noted that embodiments taught herein physically translate the sample, and keep the laser and Bragg scan mechanism stationary, while scanning the beam across the sample. Both methods are contemplated herein when using the term "translating" the medium relative to the beam.

As previously mentioned, one class of reagents which is suitable for use in conjunction with the principles of the present invention is the "OKT" brand series of monoclonal antibody reagents, which have various prescribed affinities and hence have respective capacities to identify corresponding subclasses of lymphocytes. These antibodies, their character and characteristic affinity, their preparation and their use are described in U.S. Pat. Nos. 4,363,799; 4,361,549; 4,381,295; 4,364,932; 3,364,933; 4,361,550; 4,364,934; 4,364,935; 4,364,937; 4,364,936. In general, they may be used either with a manual preparation procedure, or an automated procedure. For some tests, but a single antibody may yield adequate diagnostic results. For others, more than one antibody (e.g. with different fluorescent responses) may be used in a single test. In still other events, it is foreseen that a panel of such antibodies, each involving a respective successive test, may be utilized in accordance with the principles of the present invention in conjunction with one another to yield a specific diagnostic result in combinatorial fashion.

In a manual procedure, a series of test vials is to be selected, each having a different, characteristic antibody reagent. The patient panel is thereby formed, and a whole blood sample of predetermined size is added to each such sample vial. After a suitable incubation period, for example thirty minutes, subsequent reagents may be added, for example a lysing reagent to remove red cells. Thereupon, the processed sample is placed in a cuvette and analyzed in accordance with the principles of the present invention. For such analyses, it is noteworthy that the lysis of red cells takes place quickly, and that white cells are lysed by the same reagent at a somewhat slower rate, such that the employment of the principles of the present invention should take place in that time period, for example a two-minute interval. It will be appreciated that the rapidity and accuracy of the principles of the present invention provide most welcome relief to manual or to less rapid automated methods in accordance with the prior art.

Figure 2:
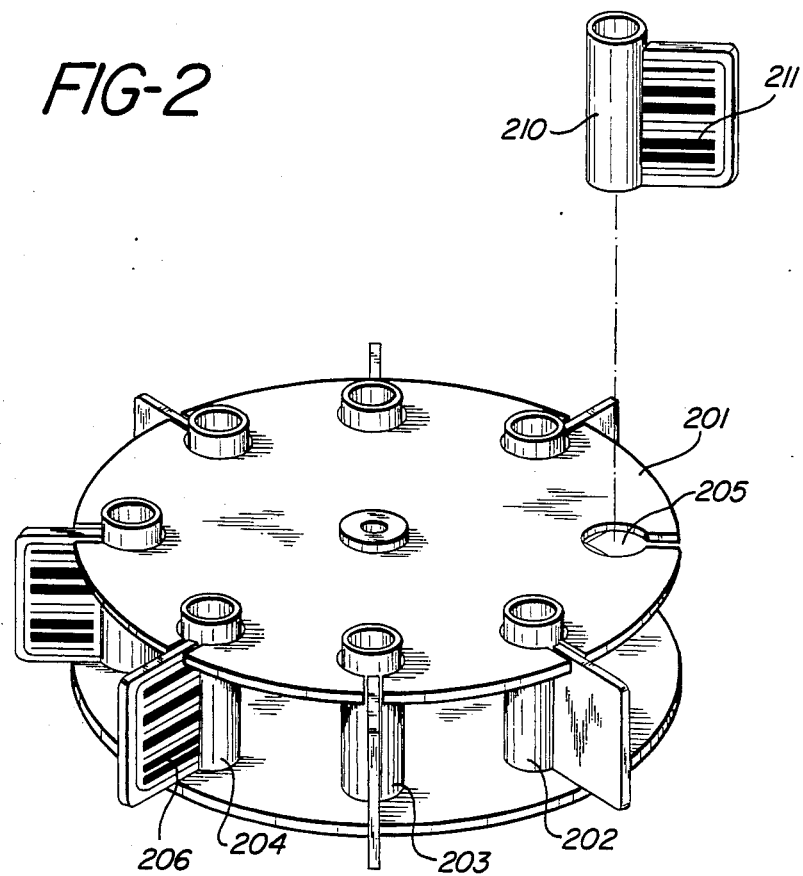
FIG. 2 shows a tray of receptacles designed for analysis of a sample with a panel of reagents in accordance with the principles of the present invention.

An automated approach to this preparation process will be evident from consideration of the exemplary fluidic system set forth in FIG. 2. In FIG. 2, a tray 201 carries a series of vials 202, 203, 204, and 210, each of which is adapted for a different, successive test. As shown in FIG. 2, each such vial has a finned handle which in turn carries indicia of the reagent and test associated therewith. Such indicia may take the form of a bar code for automated scanners, such as shown, or alternatively may take the form of various human or machine readable codes. In any event, a number of such vials constituting a panel for analysis of a sample is selected, and the entire carousel is inserted into a suitable system such as the one shown in FIG. 3. As the vial code 206, 211, etc. is read, an associated test will be designated, it being understood that samples also need be added to each vial. Assuming exemplary tests as previously described, lysing reagent is added, is incubated for a short time (e.g., 20 seconds), and the lysed sample is applied to the cuvette. The cuvette in turn is scanned, the results are noted, and the system is prepared for yet another test. In the event that a single cuvette system such as shown in FIG. 1 will be utilized, there may be total replenishment or washing of the individual cuvettes. In the event that an automated system, is to be utilized, an intermediate wash step will clean the cuvette, and the process will be repeated.

Referring next to FIG. 3, there is shown an alternative embodiment of the principles of the present invention. In essence, FIG. 3 shows a system which is somewhat more advantageously packaged, and which includes a disposable cuvette which is adapted to successive tests constituting a panel of investigations. Otherwise, however, in structure and in principle the embodiment of FIG. 3 is directly analogous to that of FIG. 1.

For compactness, the apparatus of FIG. 3 is packaged on respective supports 400 and 410, which as desired may be located directly above one another, as shown, thereby foreshortening the length of the FIG. 1 system. On the top support 400 is a laser 401, which delivers its light beam to a beam expander 402. The beam from expander 402 is coupled through a Bragg cell 403, and from there to a focusing system comprising lenses 404 and 406 and a mirror 405. The beam from the Bragg cell 403 is therefore coupled to and through a disposble sample cuvette 407.

It will be appreciated that the cuvette 407, which is a carousel in structure, includes receptacles such as 431, 432, 433, and the like which are adapted to receive and carry the sample. Peripherally disposed thereabout, are sample cuvette sections 425, 426, 427, and the like in which the prepared sample is scanned. The receptacles 431, etc. communicate with the sections 425, etc. through passageways as shown. Each such section 425, 426, etc. is of transparent constituency, such that light from the mirror 405 through lens 406 passes through the sample in the section, and thence down to the collection lens 408, a mirror 409, and to the various detectors of the FIG. 3 system. It will be seen that the sample cuvette 407 is rotatable about a central axis (e.g. by a motor, not shown), and hence that the successive sample sections are rotated (i.e. translated) through the area occupied by the beam. The Bragg cell is adapted to deflect the beam in the vertical direction shown, and hence after reflection by the mirror 405, the beam translation, and hence the scanning, occurs radially to the sample cuvette 407.

In other respects, the embodiment of FIG. 3 operates similarly to those previously described herein. That is, scatter detectors 411, 412, and 413 serve functions analagous to the scatter detectors of FIG. 1, and a lens 414 couples fluorescent emanation from cells of the sample to a fluorescence detector 415, which integrally includes both filters and detector means. The timing, control, and operation aspects of the unit, although not shown, are identical to those set forth in conjunction with the previous embodiment. That is, but for the rotation of cuvette 407 rather than direct translation of the slide form cuvette of FIG. 1, and the radial rather than vertical direction of beam scanning, the embodiment of FIG. 3 is essentially the same as that of the previous embodiments.

It is to be pointed out that the embodiments set forth herein, and the principles of the present invention, relate to the apparatus and mode of investigating the cells. It is to be understood that signals from the detectors such as 411, 412, 413 and 415 of FIG. 3 require processing in order to derive meaningful output histograms, or the like signals. To the extent that this is so, the processing and computing apparatus, the software routines, and the overall rationale therefore are at the minimum the same as those employed for like classes of cells and like reagents in flow cytometry systems. Therefore, it is anticipated that at the least, prior art flow cytometry processing and display apparatus may be utilized in accordance with the principles of the present invention. Those of ordinary skill will, based on this apparatus, have no difficulty fashioning timing and control circuitry for intermittent operation of the Bragg cell and the sample cuvettes in timed correspondence with the operation of the detectors. To the extent required to complete the disclosure hereof, then, the various flow cytometry system patents cited in the Background section hereof are incorporated by reference herein for purposes of signal processing and control apparatus.

It will be further appreciated that the foregoing has set forth preferred and illustrative embodiments of the principles of the present invention, but that numerous alternative embodiments will occur to those of ordinary skill in the art without departure from the spirit or the scope of the present invention.

We claim:

1. A method of analyzing plural characteristics of cells in a medium based on select optically stimulated characteristics associated with the cells, comprising the steps of:
    (a) scanning the medium by moving thereacross a zone of focused illumination said zone being of a size equivalent to or larger than said cells;
    (b) while scanning, monitoring the medium for occurrence of at least one select optical characteristic associated with the cells;
    (c) halting the scan upon occurrence of said select characteristic;
    (d) detecting all others of said characteristics during the halt; and
    (e) upon completion of said detecting, resuming the scanning.

2. A method as described in claim 1 wherein said method first comprises treating said cells with an optically sensitive reagent which reacts with select subclasses of said cells; wherein said select characteristics includes light scatter, and extinction; and wherein said medium is no more than approximately twenty cell diameters in depth.

3. A method as described in claim 2 wherein said reagent includes optically labelled antibody which selectively reacts with antigenic determinants associated with said select subclasses.

4. A method as described in claim 2, wherein said scanning step includes the steps of:
    (a) providing a coherent light beam to said medium;
    (b) physically translating said medium in a given direction; and
    (c) deflecting said beam at least in a direction transverse to said given direction.

5. A method as described in claim 4 wherein said deflecting step comprises passing said beam through a Bragg cell, while modulating the optical transmission characteristics of the Bragg cell.

6. A method as described in claim 4 wherein said halting step includes first halting said transverse deflection upon occurrence of said select characteristic, and then conducting further predetermined scanning of said beam relative to said medium in order to optimize interaction of said beam with the particle having caused said occurrence.

7. A method as described in claim 6 wherein said further scanning step comprises providing still further beam deflection generally in said given direction.

8. A method as described in claim 6 wherein said physical translation is substantially continuous and unabated, and wherein said further scanning results from incidence of the beam on the translating medium.

9. A system for analyzing plural characteristics of cells in a medium based on select optically stimulated parameters associated with the cells comprising:
    (a) a source of illumination focused to a spot size equivalent to or larger than said cells;
    (b) means for scanning the illumination by passing said spot over the medium;
    (c) means for monitoring said medium for at least a select one of said parameters;
    (d) means, responsive to said means for monitoring for halting said means for scanning for a predetermined time upon occurrence of said select parameters; and
    (e) means for monitoring all others of said parameters during said predetermined time.

10. A system as described in claim 9 wherein said source includes a laser, and wherein said means for scanning includes a Bragg cell for deflecting the laser beam in a first direction, and means for translating said medium transversely to said first direction.

11. A system as described in claim 10 wherein said means for scanning further includes a second Bragg cell for deflecting said beam in a direction transverse to said first direction.

12. A system as described in claim 11 wherein said first means for monitoring comprises at least one of: light extinction sensor, narrow angle light scatter sensors, wide angle light scatter sensors, fluorescence sensors, and back scatter sensors.

13. A system as described in claim 12 wherein said other means for monitoring comprises select others of said sensors.

* * * * *